US00RE34627E

United States Patent [19]

Davini

[11] E Patent Number: Re. 34,627

[45] Reissued Date of Patent: May 31, 1994

[54] SPLINT SYSTEM

[76] Inventor: Mark A. Davini, 382 Boston Turnpike, Suite 101, Shrewsbury, Mass. 01545

[21] Appl. No.: 967,993

[22] Filed: Oct. 28, 1992

Related U.S. Patent Documents

Reissue of:

[64] Patent No.: 4,966,137
Issued: Oct. 30, 1990
Appl. No.: 410,360
Filed: Sep. 19, 1989

[51] Int. Cl.[5] ..... A61F 5/00; A61F 13/00; A41D 19/02

[52] U.S. Cl. ..... 602/5; 602/21; 602/64; 2/170

[58] Field of Search ..... 602/5, 6, 13, 15, 20, 602/21, 22, 62, 63, 64; 2/20, 24, 162, 170, 167; 63/3

[56] References Cited

U.S. PATENT DOCUMENTS

| | | | |
|---|---|---|---|
| 258,111 | 5/1882 | Pervear | 63/11 |
| 686,090 | 11/1901 | Krekel | 63/3 |
| 1,189,198 | 6/1916 | Groome | 2/170 |
| 2,043,153 | 6/1936 | Cox | 128/879 |
| 2,563,818 | 8/1951 | Clendening | 63/3 |
| 2,604,629 | 7/1952 | Kennedy | 2/170 |
| 2,980,110 | 4/1961 | Brumfield et al. | 128/87 R |
| 3,086,529 | 4/1963 | Munz et al. | 128/878 |
| 3,117,786 | 1/1964 | Anderson | 128/89 R |
| 3,256,882 | 6/1966 | Huber | 602/64 |
| 3,270,742 | 9/1966 | Costa | 128/89 R |
| 3,373,445 | 3/1968 | O'Neill | 2/170 |
| 3,682,163 | 8/1972 | Plummer | 128/87 R |
| 3,726,525 | 4/1973 | Jackson | 273/54 B |
| 4,048,991 | 9/1977 | Marx | 602/64 |
| 4,087,989 | 5/1978 | Taran | 63/11 |
| 4,182,318 | 1/1980 | Beige et al. | 128/77 |
| 4,377,284 | 3/1983 | Okerlin | 128/878 |
| 4,436,088 | 3/1984 | Finnieston | 128/77 |
| 4,462,116 | 7/1984 | Sanzone | 2/170 |
| 4,538,600 | 4/1985 | Hepburn | 128/88 |
| 4,628,918 | 12/1986 | Johnson, Jr. | 128/89 R |
| 4,765,319 | 8/1988 | Finnieston et al. | 128/87 |
| 4,796,611 | 1/1989 | Wardlaw | 128/87 |
| 4,829,604 | 5/1989 | Allen et al. | 2/170 |
| 4,852,556 | 8/1989 | Groiso | 128/87 R |

FOREIGN PATENT DOCUMENTS

| | | |
|---|---|---|
| 2596980 | 10/1987 | France . |
| WO8605680 | 10/1986 | PCT Int'l Appl. . |
| 424471 | 2/1935 | United Kingdom . |

OTHER PUBLICATIONS

"RSI: Disabling disease of our time," D1 and D2, Jul. 31, 1989, Worcester Telegram & Gazette.

*Primary Examiner*—Michael A. Brown

[57] ABSTRACT

System including a clamp and bandage for use in the treatment of carpal tunnel syndrome.

10 Claims, 1 Drawing Sheet

SPLINT SYSTEM

Matter enclosed in heavy brackets [ ] appears in the original patent but forms no part of this reissue specification; matter printed in italics indicates the additions made by reissue.

*This is an application for reissue of my U.S. Pat. No. 4,966,137, issued Oct. 30, 1990 on my application Ser. No. 410,360, filed Sep. 19, 1989.*

BACKGROUND OF THE INVENTION

One of the most difficult problems encountered by chiropractic and orthopedic physicians is the successful treatment of the so-called "carpal tunnel syndrome". This syndrome is defined as a median nerve compression neuropathy at the volar (palmar) aspect of the wrist where the nerve passes beneath the transverse carpal ligament. Etiology has four mechanisms, trauma, disease processes, physiological tissue swelling, and overuse injuries. Since the space in the carpal tunnel is limited, the injury to the structures is further aggravated by friction with other elements in the tunnel. The carpal tunnel is formed by the anterior concavity of the carpal bones and the flexor retinaculum (transverse carpal ligament). It is a space that has a cross-section that is approximately oval shaped. This space is almost completely occupied by flexor tendons and the median nerve so that there is very little extra space when an injury occurs. The result is, therefore, that in this tightly constricted space, the median nerve and tendons further injure themselves by rubbing against each other. Prescribed treatment for the syndrome is, in general, to allow the swollen structures to heal up and thereby have its swelling reduced. However, since the hand is in use at all times and the structures move back and forth as the fingers and hand are articulated, it is difficult not to re-irritate the injured structures. Therefore, in the past, the treatment has been to provide a fixation of the important parts of the hand that cause the structures to move through the tunnel. The immobilization has been accomplished by the use of splints such as the "cockup splint" or by the use of a band tightly wrapped around the wrist. The difficulty with both of these methods is that there is always a certain amount of movement of the hand, fingers, etc. that takes place, so that the elements lying within the carpal tunnel are not entirely fixed, and the dimension of the carpal tunnel is not altered. Furthermore, both of these splints are very awkward, since they do limit the use of the hand which is being treated. These and other difficulties experienced with prior art devices have been obviated in a novel manner by the present invention.

It is, therefore, an outstanding object of the present invention to provide a splint system which gives improved successful treatment of the carpal tunnel syndrome.

Another object of the invention is to provide a system for treating the carpal tunnel syndrome without requiring complete immobilization of the hand and fingers.

A further object of the invention is to provide a system for enlarging the dimension of the carpal tunnel, thus allowing decompression of the involved injured structures.

A further object of the invention by enlarging the dimension of the carpal tunnel allowing decompression of the involved injured structures.

A further object of the invention is to provide a splint system that can be used to treat the carpal tunnel syndrome, but which system can be removed readily by the patient for washing and the like.

Another object of the invention is to provide a splint system for use in treating the carpal tunnel syndrome, which system is simple in construction, which is inexpensive to manufacture, and which is capable of a long life of useful service with a minimum of maintenance.

A further object of the invention is to provide a splint system which can be readily applied in the health care practitioner's office without the use of special equipment.

SUMMARY OF THE INVENTION

In general, the invention consists of a clamp formed of semi-rigid material which surrounds the wrist and is held in place by a flexible bandage. The clamp acts to press the radius and ulna bones toward one another to enlarge the carpal tunnel and allow decompression of the injured structures.

More specifically, the clamp is formed as an open tube having a generally diamond-shaped cross-section. The clamp is formed as an elongated rectangular sheet of thermoplastic resin.

DESCRIPTION OF THE PREFERRED EMBODIMENT

Figure 1:
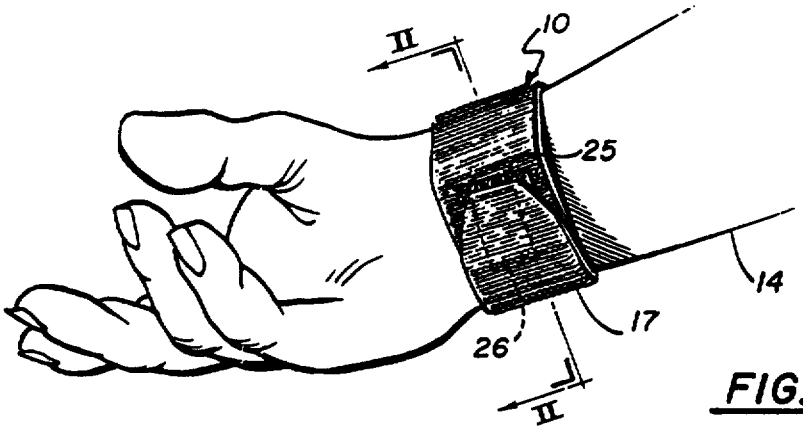
FIG. 1 is a perspective view of the splint system shown in use with a human arm.

Referring first to FIG. 1, wherein are best shown the general features of the invention, it can be seen that the splint system, indicated generally by the reference number 10, includes a bandage 17 fastened by means of a loop-and-hook system of the type known by the trademark Velcro. The bandage is shown in place on the arm 14 of a patient having the carpal tunnel syndrome.

Figure 2:
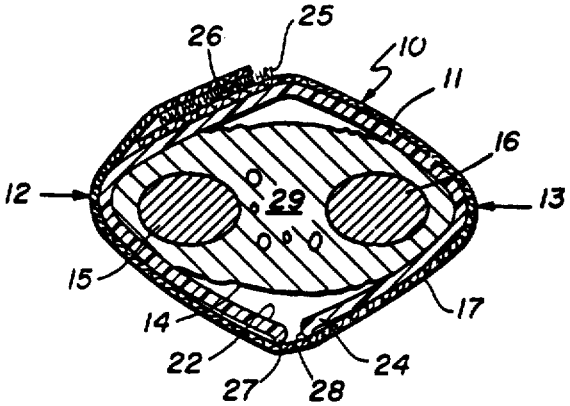
FIG. 2 is a vertical cross-sectional view of the splint system taken on the line II of FIG. 1.

Referring to FIG. 2, it can be seen that the splint system 10 used for the treatment of carpal tunnel syndrome includes a clamp 11 and the bandage 17. The clamp embraces the arm 14 of the patient and is shown in cross-section along with the ulna 16 and the radius 15. The clamp 11 is formed from a generally rectangular sheet of semi-rigid material and is formed into a generally tubular shape to give a diamond-shaped cross-sectional conformation having corners 12 and 13 located adjacent the ulna 16 and the radius 15 of the arm, respectively. In other words, the clamp 11 embraces the wrist 14 with opposite corners embracing the wrist exteriorly of the radius and the ulna bones to press them toward one another. The bandage 17 surrounds the clamp to regulate the pressure of the clamp on the wrist and to hold it in place.

Figure 3:
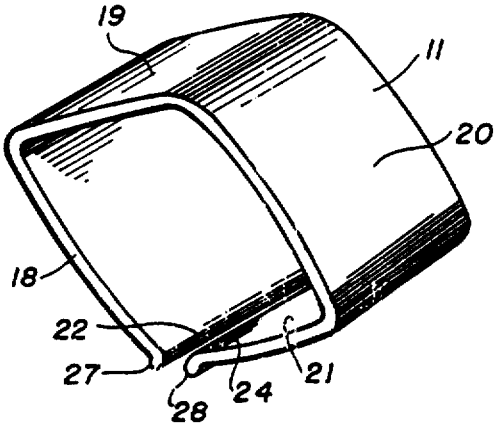
FIG. 3 is a perspective view of a clamp forming part of the splint system.

In FIG. 3 it can be seen that the clamp 11 is formed out of a thermoplastic resin such as poly-epsilon caprolactone. The clamp is formed as a tube having four panels 18, 19, 21 and 22, panel 18 being located to provide the end 22 while the panel 21 has the end 24. The end 22 is provided with a slight outward flare 27, while the end 24 is provided with a similar flare 28. As is evident in the drawing, the ends 22 and 24 are located at one corner of the general diamond shape and are spaced from one another. The other three corners of the diamond are defined by the junctions between the panels. The corners are provided with smooth curves joining the adjacent panels.

Figure 4:
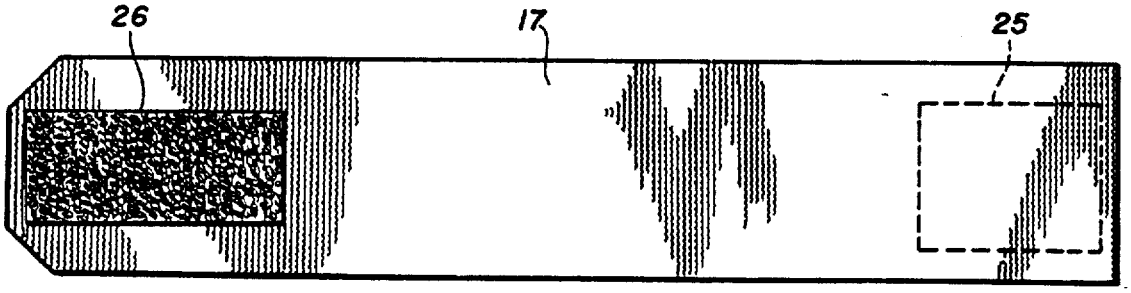
FIG. 4 is a plan view of a bandage forming part of the splint system.

As is evident in FIG. 4, the bandage 17 is of generally elongated rectangular shape and the ends can be fastened by the loop-and-hook fasteners known as Velcro located at its ends and consisting of the loop portion 26 and the hook portion 25.

The operation of the invention will now be readily understood in view of the above description. When a patient is treated in the health care practitioner's office, the clamp 11 of a suitable size is placed around his wrist and surrounding the ulna 16 and the radius 15. A certain amount of adjustment of the clamp is available when the clamp is made of poly-epsilon caprolactone because this particular resin is capable of softening at a relatively low temperature (such as 106° Fahrenheit) and remains plastic and soft even after it has cooled to a temperature (such as 110° Fahrenheit). At the lower temperature it may be brought into contact with the human skin without burning or pain. Since the resin is still soft and formable, the final shape of the diamond can be adjusted in this manner.

The bandage 17 is then wrapped around the clamp and is pulled tight enough to cause a proper compression of the arm 14 and to cause a squeezing of the radius 15 and the ulna 16 toward one another. Since the carpal tunnel (indicated generally by the reference numeral 29) lies between these two bones and contains the tendons and nerves etc. that cause the problem in the carpal tunnel syndrome, the effect is to make the tunnel larger by increasing its dimension in a line perpendicular to a line joining the centers of the ulna and the radius. This relieves any pressure that may exist in the carpal tunnel and allows the injured element to heal. At the same time that healing is taking place, the fact that the carpal tunnel dimension has been increased in this way, means that the hand can be used for normal operation without endangering the healing process.

In general, the carpal tunnel syndrome occurs when the median nerve is compressed as it passes through a narrow tunnel of bone and ligament at the wrist. This median nerve conducts sensation from part of the hand up the arm to the central nervous system. When it is compressed, the result is numbness, tingling, burning and pain in the fingers and the hand. Some of the causes of carpal tunnel syndrome include wear and tear when the lubricating lining around the tendons becomes thick and sticky due to the normal wear and tear of aging, or from repetitive hand movements, thus pressing the nerve against the tunnel. Another cause is bone dislocation and fracture due to previous dislocation or fracture of the wrist causing bone to protrude into the tunnel. Arthritis may also be present and consequently the tunnel becomes too narrow and puts pressure on the nerve. Another cause of the syndrome is fluid retention which causes swelling of the tissue in the carpal tunnel including perhaps the nerve itself. This occurs most often during pregnancy with the symptoms subsiding after the baby is born.

Obviously, minor changes may be made in the form and construction of this invention without departing from its spirit. Thus, it is not desired to confine the invention to the exact form shown and described, but it is desired to include all such as properly come within the scope claimed.

The invention having thus been described, what is claimed as new and desired to secure by Letters Patent is:

1. Splint system for the treatment of carpal tunnel syndrome in *the wrist of* a patient comprising:

(a) a clamp [formed from] *comprising* a generally rectangular sheet of semi-rigid material [and formed into] *providing* a generally tubular shape having four generally planar panels, a first two of the panels occupying the ends of the rectangular sheet, and the other two panels being located between the first two panels to give a cross-section of a diamond-shaped conformation for embracing the wrist of a patient with opposite corners embracing the wrist exteriorly of the radius and ulna bones to press [them together] *said bones towards one another*, and (b) a bandage surrounding the clamp to regulate the pressure of the clamp on the wrist.

2. Splint system as recited in claim 1, wherein the clamp is formed of a thermoplastic resin.

3. Splint system as recited in claim 2, wherein the resin is poly-epsilon-caprolactone.

4. Splint system as recited in claim 1, wherein the ends of the sheet are located at one corner of the diamond and are spaced from one another, and wherein the other three corners of the diamond are defined by the junction between the panels, the corners being formed with smooth curves.

5. Splint system as recited in claim 1, wherein the bandage is of a generally elongated rectangular shape with a loop-and-hook fastener located at its ends.

6. Splint system as recited in claim 1, wherein the ends are provided with outwardly-extending flares to prevent pinching when the ends are pressed together.

7. Splint system for the treatment of carpal tunnel syndrome *in the wrist of a patient*, comprising:

(a) a clamp [formed] of [a] semi-rigid material [and formed into] *providing* a generally tubular shape of parallelogram-shaped cross-section to give a conformation in which the clamp embraces the wrist of a patient with opposite corners embracing the wrist exteriorly of the radius and ulna bones to press [them together] *said bones towards one another*, and (b) a bandage surrounding the clamp to regulate the pressure of the clamp on the wrist.

*8. Splint system for the treatment of carpal tunnel syndrome in the wrist of a patient comprising:*

*(a) a clamp comprising a generally rectangular sheet of semi-rigid material providing at least two generally planar panels joined at a corner and adapted to embrace a side of the wrist of a patient exteriorly of one of the radius and ulna bones; and*

*(b) bandage means engaged with said clamp to regulate the pressure of the clamp on the wrist of the patient, said clamp and bandage means cooperating to apply pressure to the opposite narrow sides of the wrist of the patient to press the radius and ulna bones towards one another.*

*9. Splint system as recited in claim 8 wherein said clamp is formed of a thermoplastic resin.*

*10. Splint system as recited in claim 8, wherein said corner is formed with a smooth curve.*

* * * * *